United States Patent [19]

Fernandez et al.

[11] 4,310,618
[45] Jan. 12, 1982

[54] SILVER HALIDE PHOTOGRAPHIC MATERIAL AND PROCESS UTILIZING BLOCKED DYE-FORMING COUPLERS

[75] Inventors: Jose M. Fernandez, Rochester; Joseph P. Pepe, Penfield, both of N.Y.

[73] Assignee: Eastman Kodak Company, Rochester, N.Y.

[21] Appl. No.: 154,655

[22] Filed: May 30, 1980

[51] Int. Cl.³ .............................................. G03C 7/00
[52] U.S. Cl. .................................. 430/381; 430/384; 430/385; 430/386; 430/387; 430/388; 430/389; 430/548; 430/552; 430/553; 430/554; 430/555; 430/556; 430/557; 430/558
[58] Field of Search .............. 430/381, 386, 387, 388, 430/389, 548, 554, 555, 556, 557, 558, 384, 552, 553

[56] References Cited

U.S. PATENT DOCUMENTS

| | | |
|---|---|---|
| T887,007 | 6/1971 | Dallon et al. |
| 2,436,130 | 2/1948 | Weissberger et al. ............ 430/558 |
| 2,575,182 | 11/1951 | Martin ............................... 430/554 |
| 2,706,685 | 4/1955 | Salminen ........................... 430/558 |
| 2,865,748 | 12/1958 | Feniak et al. ..................... 430/554 |
| 3,888,680 | 6/1975 | Fujiwhara et al. ................ 430/548 |
| 4,123,281 | 10/1978 | Monbaliu et al. ................. 430/555 |
| 4,130,427 | 12/1978 | Monbaliu et al. ................. 430/557 |
| 4,157,919 | 6/1979 | Lau .................................... 430/557 |

FOREIGN PATENT DOCUMENTS

1546837  5/1979  United Kingdom .

*Primary Examiner*—J. Travis Brown
*Attorney, Agent, or Firm*—Joshua G. Levitt

[57] ABSTRACT

Novel dye-forming couplers have the structure:

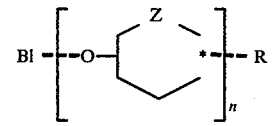

wherein:

Z represents the atoms to complete, with the attached oxygen atom, the same or different 5-pyrazolone dye-forming coupler moiety, phenol dye-forming coupler moiety or naphthol dye-forming coupler moiety, the * in the ring completed by Z representing the coupling position;

R is hydrogen or a coupling-off group;

Bl is a blocking group removable, during development, from the coupler moiety completed by Z to which it is directly attached; and n is an integer of 2 to 4.

8 Claims, No Drawings

SILVER HALIDE PHOTOGRAPHIC MATERIAL AND PROCESS UTILIZING BLOCKED DYE-FORMING COUPLERS

This invention relates to novel dye-forming couplers, to photographic silver halide emulsions and elements containing these couplers, to processes of forming dye images with elements containing these couplers, and to processed elements containing dyes derived from these couplers.

Color images are customarily obtained in the photographic art by reaction between the oxidation product of a silver halide color-developing agent (i.e., oxidized aromatic primary amino developing agent) and a dye-forming compound known as a coupler. The reaction between coupler and oxidized color-developing agent results in coupling of the oxidized color-developing agent at a reactive site in the coupler, known as the coupling position, and yields a dye. The dyes produced by coupling are indoaniline, azomethine, indamine or indophenol dyes, depending upon the chemical composition of the coupler and the developing agent. The substractive process of color formation is ordinarily employed in multicolored photographic elements and the dyes produced by coupling are usually cyan, magenta and yellow dyes which are formed in or adjacent silver halide emulsion layers sensitive to radiation absorbed by the image dye, i.e., silver halide emulsion layers sensitive to the red-, green-or blue regions of the spectrum.

The couplers typically employed to produce magenta dyes are 5-pyrazolones, while the couplers typically employed to produce cyan dyes are phenols or naphthols. The pyrazolones yield azomethine dyes upon coupling with oxidized aromatic primary amino developing agents and the phenols and naphthols yield indoaniline dyes. In such couplers, the coupling position, i.e., the site at which oxidized color-developing agent reacts, is the active methylene group in the 4-position of the coupler. This active methylene group can be substituted or unsubstituted.

Many of the color-forming couplers employed in photographic materials are 4-equivalent couplers. In other words, they require development of four molecules of silver halide in order ultimately to produce one molecule of dye. Also known are 2-equivalent couplers which require development of two molecules of silver halide to produce one molecule of dye.

We have found a novel class of dye-forming couplers. These couplers comprise two or more 5-pyrazolone coupler moieties, phenol coupler moieties or naphthol coupler moieties in which the oxygen atom of the first coupler moiety is blocked and the coupling position of that coupler moiety is joined to the oxygen atom of the second coupler moiety. This sequence of attachment is repeated until the last coupler moiety (which can be the second coupler moiety) is reached. Its coupling position is unsubstituted or substituted with a coupling-off group.

Blocking the oxygen atom deactivates the coupling position. Thus, the coupler moieties cannot react with oxidized color-developing agent until the blocking group is removed, thereby activating the coupling position. The blocking group is chosen so that it is removable during photographic development. Once the blocking group is removed, the coupler moieties react with oxidized color developing agent sequentially, reaction of the first coupler moiety unblocks the second coupler moiety permitting it to react with oxidized color-developing agent, and so on until all of the coupler moieties of a given coupler have reacted with oxidized color-developing agent, or until oxidized color-developing agent is locally unavailable, or until the development step is terminated.

In one aspect this invention relates to dye-forming couplers having the structure:

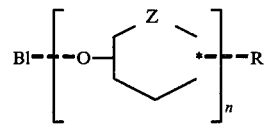

wherein:

Z represents the atoms to complete, with the attached oxygen atom, the same or different 5-pyrazolone magenta dye-forming coupler moiety, phenol cyan dye-forming coupler moiety or naphthol cyan dye-forming coupler moiety, the * in the ring completed by Z representing the coupling position;

R is hydrogen or a coupling-off group;

Bl is a blocking group removable, during development, from the coupler moiety completed by Z to which it is directly attached to thereby activate the coupling position of the coupler moiety; and n is an integer of 2 to 4.

In another aspect, this invention relates to photographic silver halide emulsions and elements containing dye-forming couplers as described above.

In yet another aspect, this invention relates to processes of forming dye images in a photographic element by developing the element in the presence of a dye-forming coupler as described above.

In still another aspect, this invention relates to processed photographic elements containing dye images obtained by coupling of oxidized silver halide color-developing agent and a coupler as described above.

The coupler moiety represented by Z can be derived from any 5-pyrazolone magenta dye-forming coupler, phenol cyan dye-forming coupler or naphthol cyan dye-forming coupler. Preferably each moiety is the same, although different coupler moieties can be used in the same coupler, if desired. Although the coupler moieties can contain conventional ballast groups, because of the bulk provided by joining two or more coupler moieties together the ballast group can be reduced in size or eliminated, if desired.

Representative 5-pyrazolone couplers, from which the coupler moiety Z can be derived, are described in U.S. Pat. Nos. 2,343,703, 2,369,489, 2,600,788, 2,908,573, 3,062,653, 3,152,896 and 3,519,429. Typical 5-pyrazolone coupler moieties can be represented by the structures:

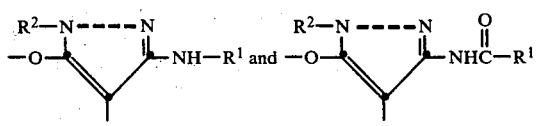

where each of $R^1$ and $R^2$ is, individually, alkyl of 1 to 40 carbon atoms or aryl of 6 to 40 carbon atoms and include such substituteents as alkyl, aryl, alkoxy, aryloxy, alkylthio, arylthio, hydroxy, halogen, cyano, alkoxycarbonyl, aryloxycarbonyl, carboxy, acyl, acyloxy, carbonamido, carbamoyl, alkylsulfonyl, arylsulfonyl, sulfonamido and sulfamoyl.

Representative phenol and naphthol couplers, from which the coupler moiety Z can be derived, are described in U.S. Pat. Nos. 2,367,531, 2,423,730, 2,474,293, 2,772,162, 2,895,826, 3,002,836 and 3,041,236. Typical phenol and naphthol coupler moieties can be represented by the structures:

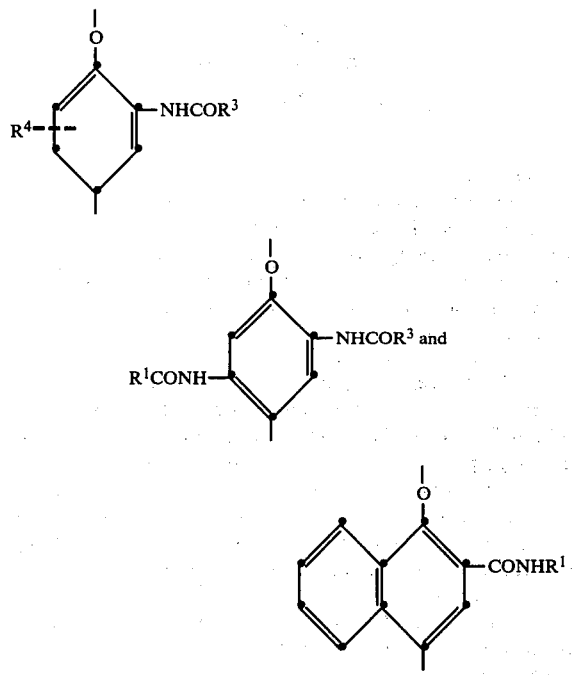

where $R^1$ is as defined above, $R^3$ is $R^1$ or $-NHR^1$, and $R^4$ represents one or more halogen atoms or alkyl or alkoxy groups containing 1 to 10 carbon atoms.

The coupling-off group represented by R can be any of the coupling-off groups known in the art. Such groups can alter the equivalency of the coupler, can modify the reactivity of the coupler, or can advantageously affect the layer in which the coupler is coated or other layers in the element by performing, after release from the coupler, such functions as development inhibition, bleach inhibition, bleach acceleration, color correction and the like. Representative coupling-off groups include halogen, alkoxy, aryloxy, hetercycloxy, sulfonyloxy, acyloxy, acyl, heterocyclyl, thiocyano, alkylthio, arylthio, heterocyclylthio, sulfonamido, phosphonyloxy and arylazo.

The blocking group represented by Bl can be any group which is removable from the oxygen atom of the first coupler moiety during development. Techniques for removing the blocking group include hydrolysis, coupling and intramolecular nucleophilic displacement.

Typical groups removable by hydrolysis include the acyl groups described in U.S. Pat. Nos. 2,575,182, 2,706,685, 2,865,748 and 4,123,281, such as aliphatic and aromatic carbonyl and sulfonyl groups.

Typical groups removable by coupling include any coupler moiety which, upon reaction with oxidized color-developing agent, ultimately yields (1) a reaction product which is soluble in alkaline processing solutions, so that during processing it is removed from the element, or (2) a colorless reaction product, so that it does not contribute to final image density. Typical coupling moieties which yield alkali-soluble reaction products are yellow and cyan dye-forming couplers which contain acid and/or ester groups thereby to confer alkali solubility upon the reaction product. Typical coupling moieties which yield colorless reaction products are described in such patents as U.K. Patent 861,138 and U.S. Pat. Nos. 3,632,345, 3,928,041, 3,958,993 and 3,961,959 which relate to carbonyl-containing compounds which form colorless products on reaction with oxidized color-developing agent. It will be appreciated that, when the blocking group is a coupler moiety, it is joined via its coupling position to the remainder of the coupler.

Typical groups which are removable by intramolecular nucleophilic displacement are described in the commonly assigned application of Jared B Mooberry and William C Archie, Jr, U.S. Ser. No. 949,462 filed Oct. 10, 1978, the disclosure of which is incorporated herein by reference. Such groups can be represented by the structure:

$$-E^1-X-NuP$$

wherein:

$E^1$ is an electrophilic group;

NuP is a precursor of a nucleophilic group which, under alkaline conditions, is converted uniformly to a nucleophilic group; and X is a linking group for spatially relating $E^1$ and NuP to enable them to undergo, after conversion of NuP to a nucleophilic group, an intramolecular nucleophilic displacement reaction which cleaves the bond between $E^1$ and the oxygen atom to which it is joined.

Preferred couplers are those in which the coupler moiety Z is a 5-pyrazolone coupler moiety and the blocking group Bl is a coupler moiety which reacts with oxidized color-developing agent ultimately to yield a colorless or alkali-soluble reaction product. As described in the commonly assigned application of Thomas E Gompf, Howell A Hammond and Jared B Mooberry, Serial No. 124,872 filed Feb. 26, 1980, entitled Blocked Pyrazolone Magenta Dye-Forming Couplers, 5-pyrazolone couplers blocked in this manner have both good reactivity and good resistance to aerial contaminants.

Preferred such couplers can be represented by the structural formula:

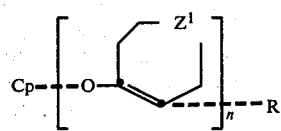

wherein:

$Z^1$ represents the atoms to complete, with the attached oxygen atom, a 5-pyrazolone magenta dye-forming coupler moiety as described above;

R is hydrogen or a coupling-off group as defined above;

n integer of 2 to 4; and

Cp is a coupler moiety which, upon reaction with oxidized color-developing agent, yields a colorless or alkali-soluble reaction product, as described above.

Especially preferred couplers are blocked with alkali-soluble, yellow dye-forming coupler moieties and can be represented by the structure:

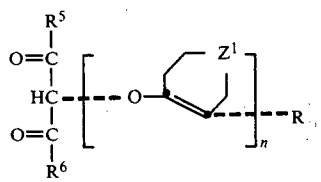

wherein:

$Z^1$, R and n are as defined above and $R^5$ and $R^6$ represent the atoms to complete an alkali-soluble, yellow dye-forming coupler moiety. Representative $R^5$ groups are alkyl, such as t-butyl, and aryl, such as phenyl and alkoxyphenyl. Representative $R^6$ groups are phenylamino groups containing acid or ester solubilizing groups such as carboxy and sulfo groups.

Representative couplers of this invention have the structures:

Coupler I

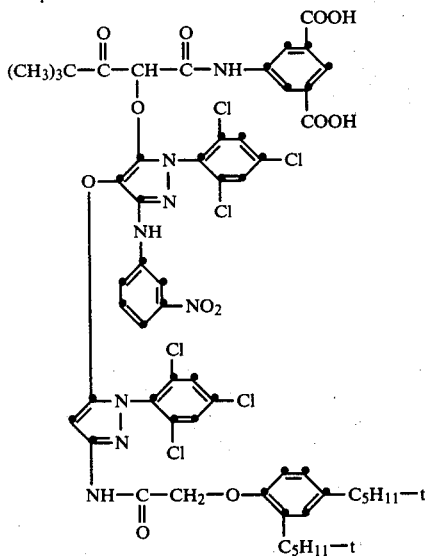

Coupler II

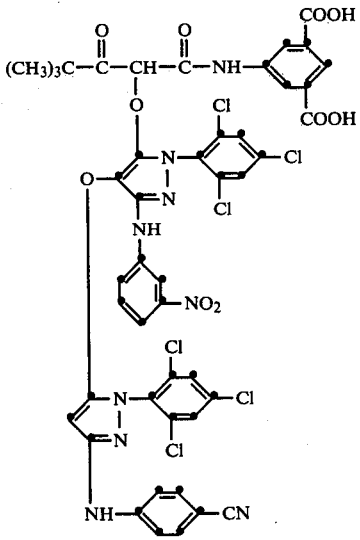

Coupler III

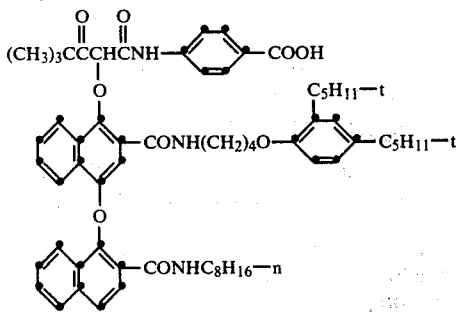

Coupler IV

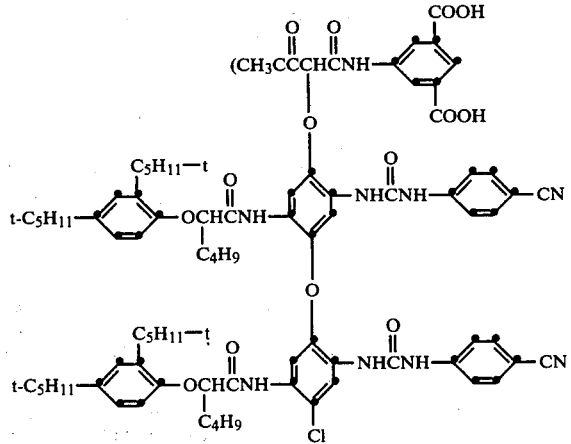

Coupler V

Coupler VI

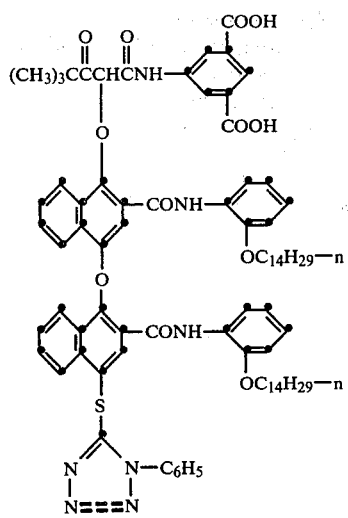

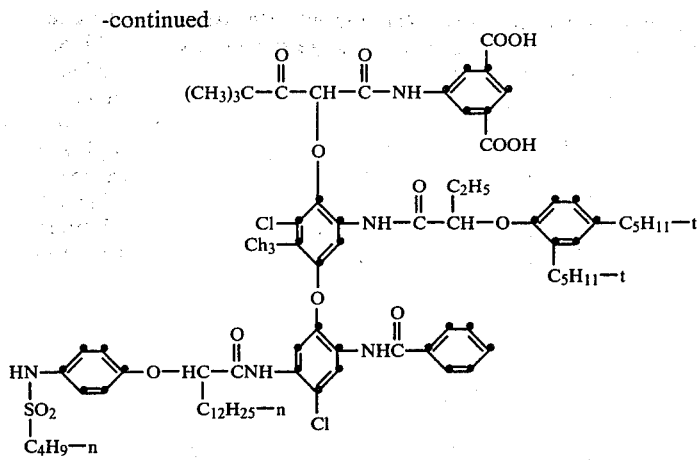

-continued

Coupler VII

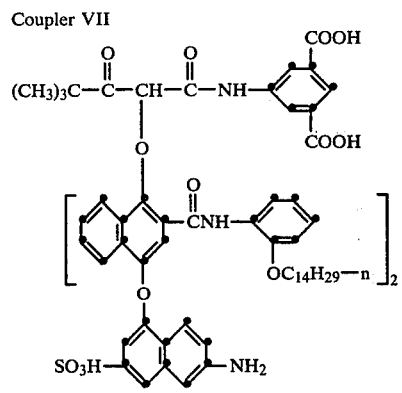

Coupler VIII

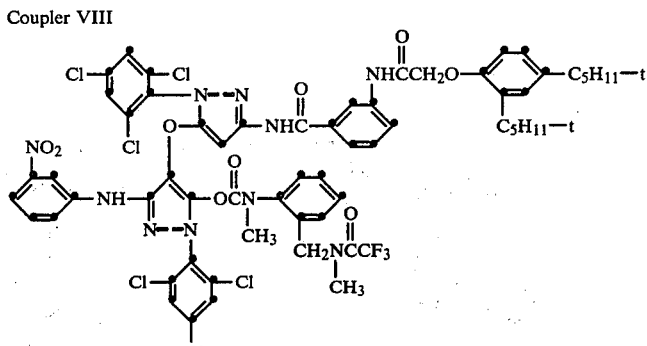

Couplers of this invention can be prepared by condensing a 5-pyrazolone coupler, a 1-naphthol coupler or a 1-phenol coupler with either (a) 2-halo-1,3-diester, the product of which can be condensed with an isocyanide dichloride and hydrazine to give a 4-pyrazolyloxy-5-pyrazolone, a 4-naphthoxy-5-pyrazolone or a 4-phenoxy-5-pyrazolone, respectively, whose enol site can then be blocked with an appropriate blocking group by techniques known in the art, or (b) an appropriate 4-halo phenolic or naphtholic moiety, the free hydroxyl of which can be blocked with an appropriate blocking group by techniques known in the art.

The couplers of this invention can be used in the ways and for the purposes that dye-forming couplers are used in the photographic art.

Typically, the couplers are incorporated in silver halide emulsions and the emulsions coated on a support to form a photographic element. Alternatively, the couplers can be incorporated in photographic elements adjacent the silver halide emulsion where, during development, the coupler will be in reactive association with development products such as oxidized color-developing agent. Thus, as used herein, the term "associated with" signifies that the coupler is in the silver halide emulsion layer or in an adjacent location where, during processing, it will come into reactive contact with silver halide development products.

The photographic elements can be single-color elements or multicolor elements. In a multicolor element, the dye-forming couplers of this invention would usually be associated with an emulsion primarily sensitive to radiation absorbed by the dye formed from the coupler, although they could be associated with an emulsion sensitive to a different region, or regions, of the spectrum. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer, e.g., as by the use of microvessels as described by Whitmore, U.S. Patent Application Ser. No. 008,819 filed Feb. 2, 1979, now abandoned.

A typical multicolor photographic element would comprise a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler, at least one of the dye-forming couplers being a coupler of this invention. The element can contain additional layers, such as filter layers, interlayers, overcoat layers, subbing layers and the like.

In the following discussion of suitable materials for use in the emulsions and elements of this invention, reference will be made to *Research Disclosure*, December, 1978, Item 17643, published by Industrial Opportunities Ltd, Homewell Havant, Hampshire, PO9 1EF, UK, the disclosures of which are incorporated herein by reference. This publication will be identified hereafter as *Research Disclosure*.

The silver halide emulsions employed in the elements of this invention can be either negative-working or positive-working. Suitable emulsions and their preparation are described in *Research Disclosure*, Sections I and II, and the publications cited therein. Suitable vehicles for the emulsion layers and other layers of elements of this invention are described in *Research Disclosure*, Section IX, and the publications cited therein.

In addition to the couplers of this invention, the elements of the invention can include additional couplers as described in *Research Disclosure*, Section VII, paragraphs D, E, F and G, and the publications cited therein. These couplers and any additional couplers can be incorporated in the elements and emulsions as described in *Research Disclosure*, Section VII, paragraph C, and the publications cited therein.

The photographic elements of this invention or individual layers thereof, can contain brighteners (see *Research Disclosure*, Section V), antifoggants and stabilizers (see *Research Disclosure*, Section VI), antistain agents and image dye stabilizer (see *Research Disclosure*, Section VII, paragraphs I and J), light-absorbing and -scattering materials (see *Research Disclosure*, Section VIII), hardeners (see *Research Disclosure*, Section XI), plasticizers and lubricants (see *Research Disclosure*, Section XII), antistatic agents (see *Research Disclosure*, Section XIII), matting agents (see *Research Disclosure*, Section XVI) and development modifiers (see *Research Disclosure*, Section XXI).

The photographic elements can be coated on a variety of supports as described in *Research Disclosure*, Section XVII, and the references described therein.

Photographic elements can be exposed to actinic radiation, typically in the visible region of the spectrum, to form a latent image as described in *Research Disclosure*, Section XVIII, and then processed to form a visible dye image as described in *Research Disclosure*, Section XIX. Processing to form a visible dye image includes the step of contacting the element with a color-developing agent to reduced developable silver halide and oxidize the color-developing agent. Oxidized color-developing agent in turn reacts with the coupler to yield a dye.

Preferred color-developing agents are p-phenylenediamines. Especially preferred are 4-amino-N,N-diethylaniline hydrochloride, 4-amino-3-methyl-Nethyl-N-$\beta$-(methanesulfonamido)ethylaniline sulfate hydrate, 4-amino-3-methyl-N-ethyl-N,N-diethylaniline sulfate, 4-amino-3-$\beta$-(methanesulfonamido)ethyl-N,N-diethylaniline hydrochloride and 4-amino-N-ethyl-N-(2-methoxyethyl)-m-toluidine di-p-toluene sulfonic acid.

With negative-working silver halide, this processing step leads to a negative image. To obtain a positive (or reversal) image, this step can be preceded by development with a nonchromogenic developing agent to develop exposed silver halide, but not to form dye, and then uniform fogging of the element to render unexposed silver halide developable. Alternatively, a direct-positive emulsion can be employed to obtain a positive image.

Development is followed by the conventional steps of bleaching, fixing or bleach-fixing, to remove silver and silver halide, washing and drying.

The following examples further illustrate this invention.

EXAMPLE 1

Preparation of Coupler I

Step 1

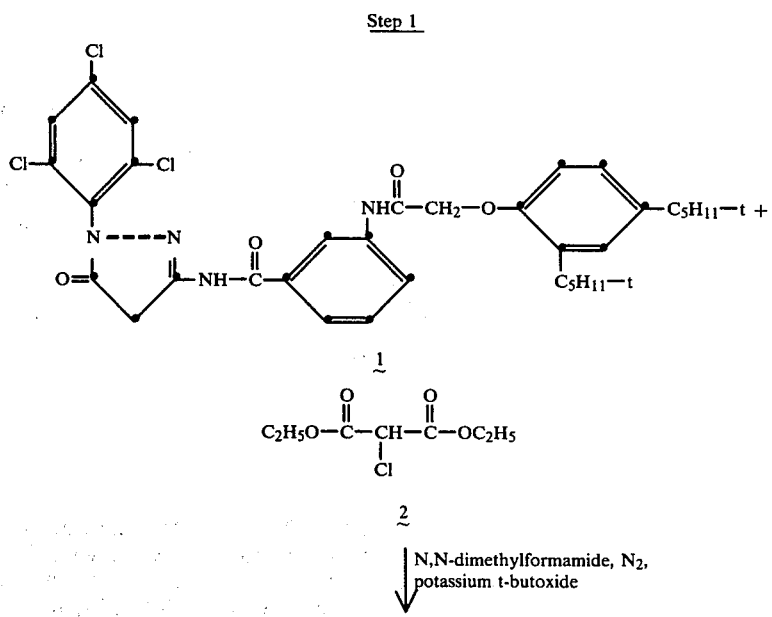

Step 1

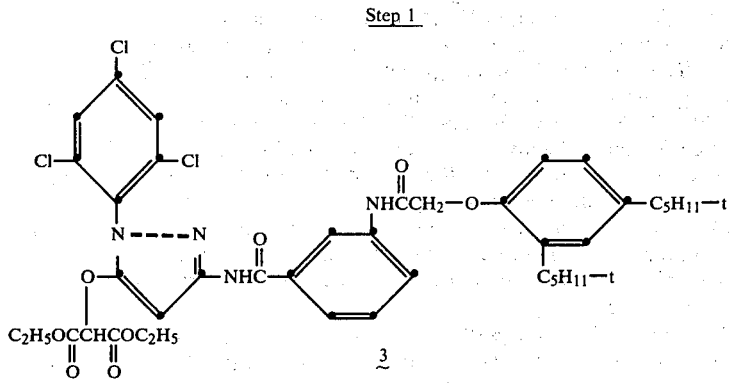

In dry N,N-dimethylformamide (150 ml), 1-(2,4,6-trichlorophenyl)-3-[3-(2,4-di-t-pentylphenoxyacetamido)-benzamido]-5-pyrazolone (19.1 g, 0.030 mole) was dissolved and the solution stirred under nitrogen. Potassium t-butoxide (3.4 g, 0.030 mole) was added, followed several minutes later by diethylchloromalonate (5.8 g, 0.030 mole). The mixture was stirred for 2 hr at 40° C. and then overnight at room temperature. The solution was poured into an ice-water mixture (500 g of each) which had been acidified with glacial acetic acid (30 ml). The off-white solid precipitate was collected, washed with water and dried in vacuo at 50° C.; 22 g (88%). The product could be obtained pure by high-pressure liquid chromatography.

cooled to 10° C. and m-nitrophenylisocyanide dichloride (1.1 g, 0.0050 mole) in tetrahydrofuran (20 ml) was added. The reaction mixture was stirred for 2 hr at room temperature and then 2,4,6-trichlorophenylhydrazine (1.0 g, 0.0050 mole) in methanol (50 ml) was added, followed in 10 min by sodium methoxide (0.60 g, 0.011 mole). Stirring was continued for 30 min and the reaction mixture was then slowly poured, with stirring, to an ice-water mixture (200 g of each) which had been acidified with glacial acetic acid (20 ml). A gray solid product was collected, washed with water, and dried under nitrogen; yield 5.2 g (97%). The product was purified by high-pressure liquid chromatography (silica, chloroformethyl acetate at 4:1); mp 162°–165° C. (dec).

Step 2

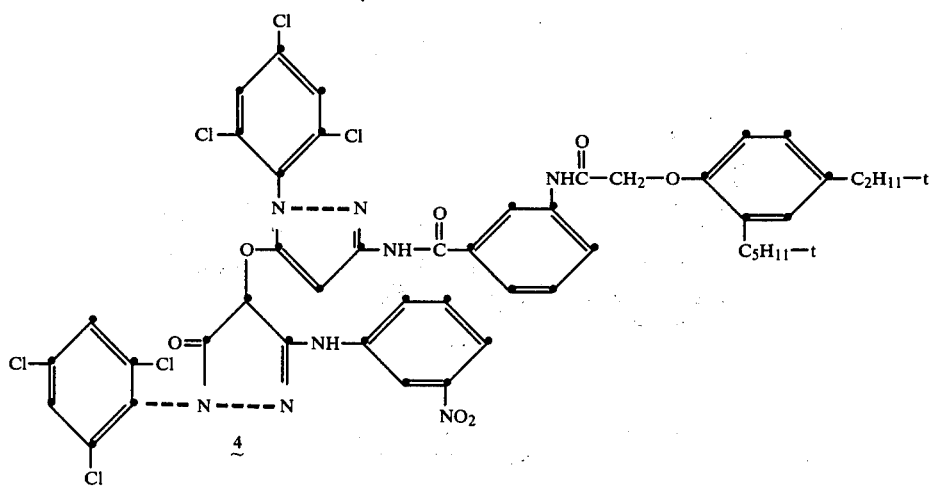

The purified enol ether pyrazolone (3) (4.2 g, 0.0050 mole) was dissolved in dry tetrahydrofuran (50 ml) under nitrogen. With stirring, potassium t-butoxide (0.60 g, 0.0055 mole) was added. The solution was The nmr spectrum was consistent with the structure.

Calculated for $C_{49}H_{44}Cl_6N_8O_7$: C, 55.2%; H, 4.1%; Cl, 19.8%; N, 9.6%. Found: C, 55.3%; H, 4.0%; Cl, 18.4%; N, 10.0%.

Step 3

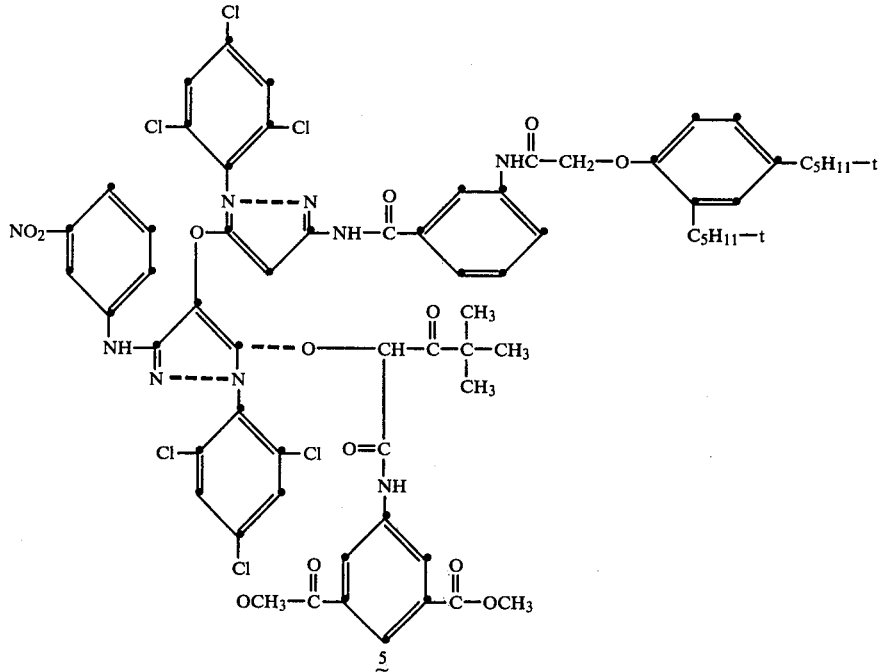

The product of Step 2, (4) (4.5 g, 0.0042 mole), was dissolved in dry N,N-dimethylformamide and potassium t-butoxide (0.50 g, 0.0050 mole) was added followed shortly by the α-chloro-α-pivaloylacetanilide (1.6 g, 0.0050 mole). After 4 days of stirring at room temperature, the reaction mixture was poured into ice water (300 ml) to which glacial acetic acid (10 ml) had been added. An orange-colored solid was collected, washed and dried; yield, 5.7 g (96%). The product was purified by high-pressure liquid chromatography; mp 162°–166° C. (dec). The nmr spectrum was consistent with the structure.

Calculated for $C_{66}H_{63}Cl_6N_9O_{13}$: C, 56.4%; H, 4.5%; Cl, 9.0%, N, 16.3%. Found: C, 56.6%; H, 4.5%; Cl, 9.0%; N, 14.9%.

Step 4

5
|
ethanol, dimethylsulfoxide, sodium hydroxide, water
↓

Step 4

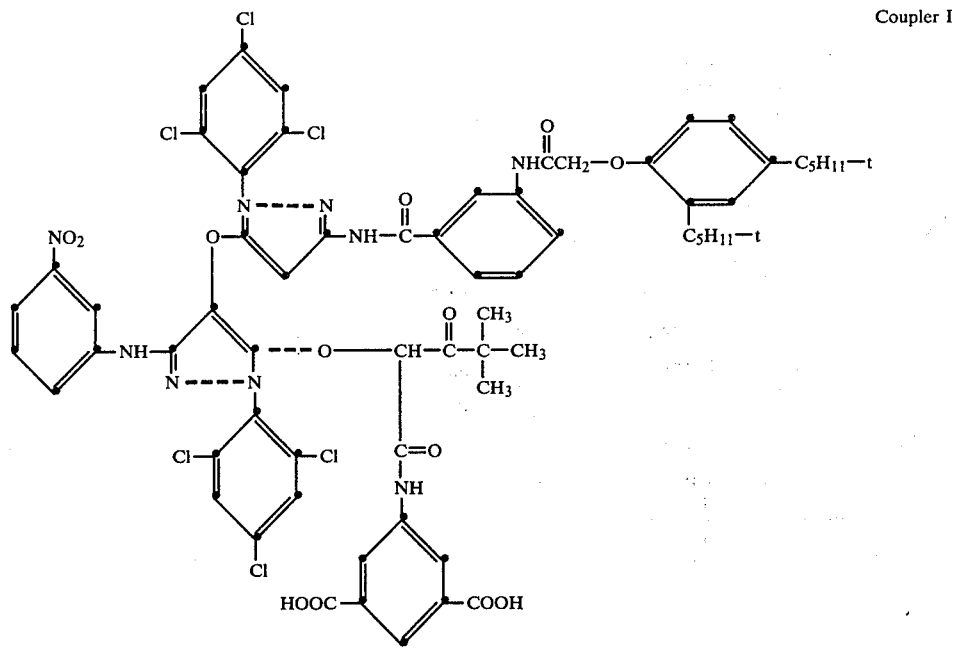

The product of Step 3 (5), (2.3 g, 0.0016 mole) was dissolved in ethanol (20 ml) and dimethylsulfoxide (16 ml). Aqueous 50% sodium hydroxide (4 ml) was added, and the reaction mixture stirred at room temperature for 25 min. The solution was dumped into an ice-water mixture (200 g of each) which had been acidified with glacial acetic acid (20 ml). The precipitate was collected, washed with water and dried under nitrogen; yield, 1.7 g (75%). Column chromatography (silica, ethyl acetate) gave 0.60 g of pure product; mp 172°–178° C. (dec). The nmr was consistent with the structure.

Calculated for $C_{64}H_{59}Cl_6N_9O_{13}$: C, 55.9%; H, 4.3%; Cl, 15.5%; N, 9.2%. Found: C, 56.3%; H, 4.7%; Cl, 15.5%; N, 8.9%.

EXAMPLE 2

Preparation of Coupler II

Step 1

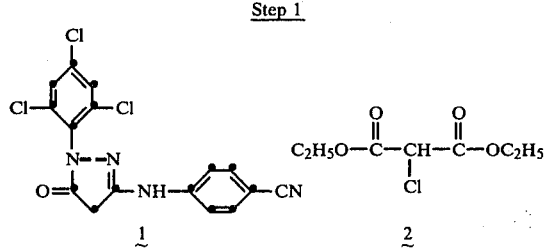

N,N-dimethylformamide, $N_2$, potassium t-butoxide, 60° C.

-continued
Step 1

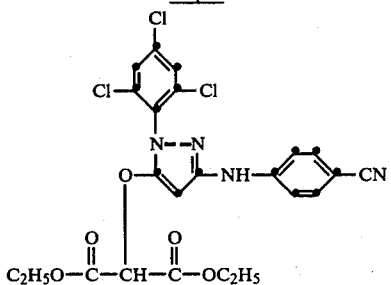

In dry N,N-dimethylformamide (250 ml), 1-(2,4,6-trichlorophenyl)-3-(p-cyanoanilino)-5-pyrazolone (37.96 g, 0.100 mole) was dissolved, and the solution was stirred under nitrogen. Potassium t-butoxide (90%) (12.47 g, 0.100 mole) was added, followed in 20 min by diethylchloromalonate (96%) (20.27 g, 0.100 mole). The stirred reaction mixture was warmed to 60° C. and kept there for 5½ hr. The solution was poured, with stirring, into 2 liters of ice water where a pink solid precipitated. This was collected, airdried for several hours, and then dissolved in ethyl acetate (1 liter). After drying ($Na_2SO_4$) and filtration, the solution was evaporated to a brown oil which was crystallized from toluenecyclohexane and then pure toluene to give 27.5 g (51%) of a tan solid; mp 136°–140° C. The nmr spectrum was consistent with the proposed structure.

Step 2

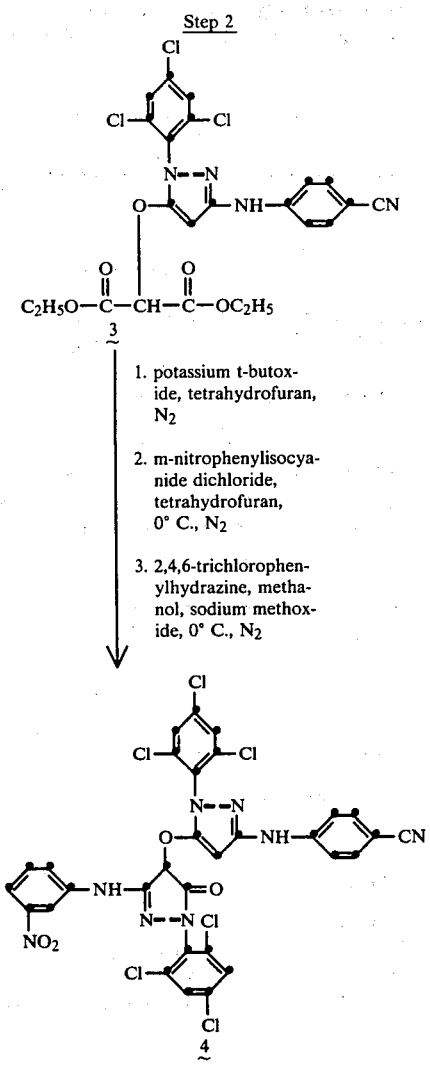

Potassium t-butoxide (95%) (2.36 g, 0.0200 mole) was added to a stirred tetrahydrofuran (200 ml) solution of the product of Step 1, (3) (10.76 g, 0.0200 mole). Under nitrogen, this solution was added dropwise (1.5 hr) to a stirred, cooled (0° C.) tetrahydrofuran (150 ml) solution of m-nitrophenylisocyanide dichloride (4.38 g, 0.0200 mole). After 1 hr, the cooling bath was removed and the mixture stirred an additional 1½ hr at room temperature. The solution was again cooled to 0° C. and 2,4,6-trichlorophenylhydrazine (4.23 g, 0.0200 mole) was added, followed in 15 min by methanol (100 ml) and sodium methoxide (95%) (2.27 g, 0.0400 mole). After 30 min, the reaction was poured, with stirring, into an ice-water mixture (2 liters) which had been acidified with glacial acetic acid (200 ml). Aqueous saturated sodium chloride (500 ml) was added, causing the rusty, brown, sticky solid product to float. Most was collected by skimming the solution and the remainder obtained by extraction with methylene chloride (2×250 ml). The product fractions were combined and the total extract washed with water (400 ml), dried (Na$_2$SO$_4$), filtered and evaporated to a brown foam. The product was dissolved in 5:1 toluene-tetrahydrofuran (600 ml) and this solution was cooled to 0° C. where the product was precipitated by the slow addition of cyclohexane. It was collected, washed with cyclohexane and vacuum-dried; yield, 10.27 g (66% of light-brown solid which was unstable to air, especially in solution.

Step 3

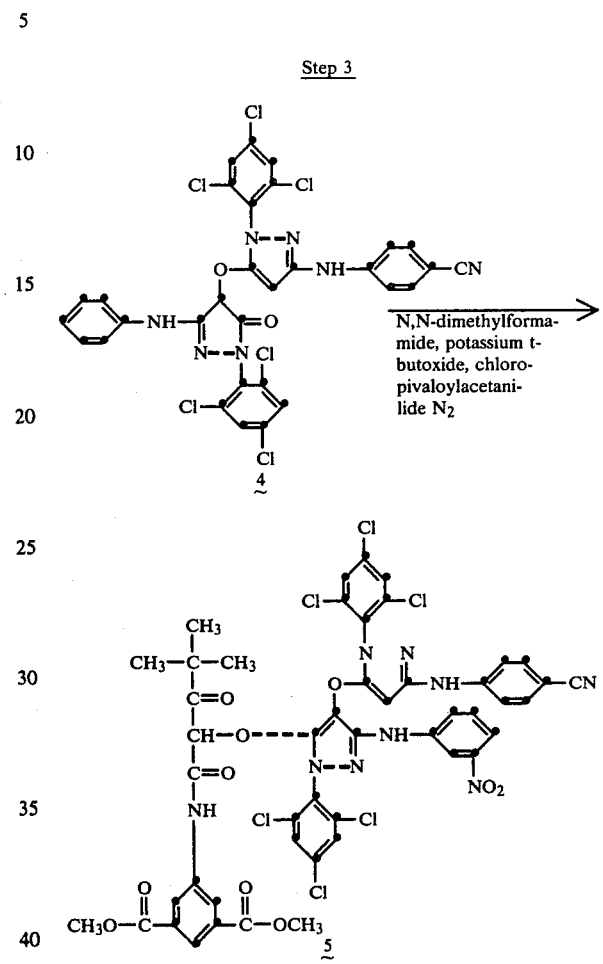

The product of Step 2, (4) (10.0 g, 0.013 mole), was dissolved in dry N,N-dimethylformamide (100 ml) under a nitrogen atmosphere. Potassium t-butoxide (95%) (1.52 g, 0.013 mole) was added and the solution then stirred for 1.25 hr while warming to room temperature. The chloropivaloylacetanilide yellow coupler (4.76 g, 0.013 mole) was added and the solution stirred at room temperature for 5 days, after which it was poured with stirring into an ice-water mixture (1500 g) which had been acidified with glacial acetic acid (100 ml). Aqueous saturated sodium chloride (500 ml) was added and the pink-colored precipitate collected, washed with water and vacuum-dried; yield, 13.18 g (91%) of crude product. The pure compound was obtained as a green solid by column chromatography (20:1 methylene chloride-ethyl acetate, silica).

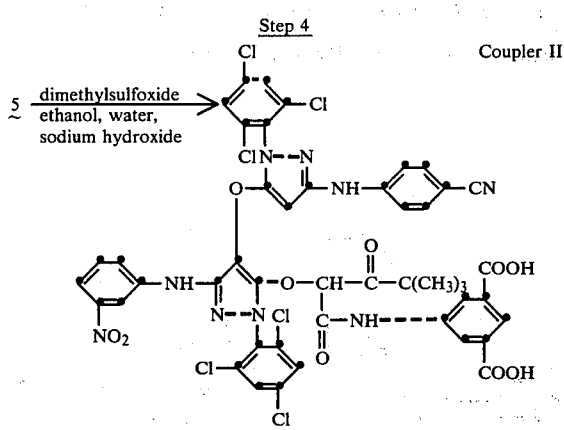

Step 4
dimethylsulfoxide, ethanol, water, sodium hydroxide → Coupler II

The product of Step 3 (5) (4.0 g, 0.0036 mole) was dissolved in a 1:1 mixture (130 ml) of absolute ethanol and dimethylsulfoxide. Aqueous 50% sodium hydroxide (16 ml) was added and the solution stirred for exactly 30 min at room temperature. The reaction mixture was poured into ice water (1500 ml) which had been acidified with glacial acetic acid (150 ml). The fine, yellowish-brown precipitate was collected, washed with water and vacuum-dried; yield, 3.47 g (89%) of crude product. Pure product was obtained by column chromatography (4:1 tetrahydrofuran-ethyl acetate, silica), followed by recrystallization from ether-hexanes; mp 195° C. (dec). The nmr spectrum was consistent with the structure.

Calculated for $C_{46}H_{31}Cl_6N_9O_{10}$: C, 51.0%; H, 2.9: N, 11.6%; Cl, 19.7%. Found: C, 50.8%; H, 3.4%; N, 12.2%; Cl, 19.0%.

EXAMPLE 3

Photographic elements were prepared by coating a cellulose acetate film support with (1) a photosensitive layer containing a silver bromoiodide emulsion at 1.6 g Ag/m$^2$, gelatin at 3.2 g/m$^2$, and one of the following couplers dispersed in an equal weight of tricresyl phosphate, and (2) an overcoat layer containing gelatin at 1.1 g/m$^2$ and bis-vinylsulfonylmethyl ether at 1.75 weight percent based on total gelatin. The couplers of the invention were coated at ½ the molar level of the control couplers because they can form two dye molecules for each coupler molecule.

| Element | Coupler | Coupler Conc (mole/m$^2$) |
|---|---|---|
| 1 | I | $2.6 \times 10^{-4}$ |
| 2 (control) | C-1 | $5.3 \times 10^{-4}$ |
| 3 | II | $2.6 \times 10^{-4}$ |
| 4 (control) | C-1 | $5.3 \times 10^{-4}$ |

Coupler C-1 has the structure:

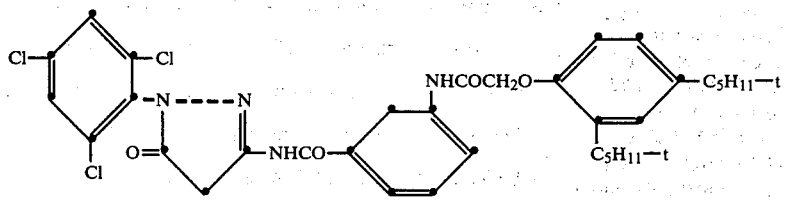

Each element was imagewise-exposed through a graduated density test object and processed in a conventional process described in *The British Journal of Photography Annual*, 1978, pp 204–206. The dye density and contrast of each element were measured with the following results:

| Element | Density Dmax | Density Dmin | Contrast (γ) |
|---|---|---|---|
| 1 | 1.10 | 0.12 | 1.01 |
| 2 | 0.86 | 0.12 | 0.60 |
| 3 | 1.18 | 0.12 | 1.12 |
| 4 | 0.92 | 0.122 | 0.62 |

From these results, it is evident that couplers of this invention yielded higher dye density and greater contrast than the control even though equivalent amounts of coupler were employed.

EXAMPLE 4

Photographic elements were prepared as described in Example 3 except that the couplers were coated at the following concentrations so as to match closely the control elements in density and contrast.

| Element | Coupler | Coupler Conc (mole/m$^2$) |
|---|---|---|
| 5 | I | $1.56 \times 10^{-4}$ |
| 6 (control) | C-1 | $5.3 \times 10^{-4}$ |
| 7 | II | $1.58 \times 10^{-4}$ |
| 8 (control) | C-1 | $5.3 \times 10^{-4}$ |
| 9 (control) | C-2 | $5.3 \times 10^{-4}$ |

Coupler C-2 has the structure:

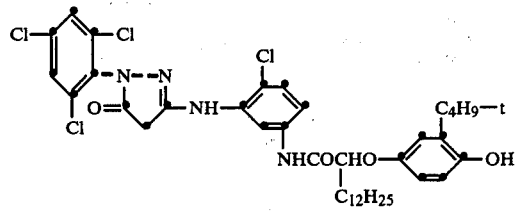

Each element was exposed and processed as described in Example 2. The dye densities and contrast of each sample were measured with the following results:

| Element | Density Dmax | Density Dmin | Contrast (γ) |
|---|---|---|---|
| 5 | 0.76 | 0.10 | 0.53 |
| 6 | 0.84 | 0.11 | 0.47 |
| 7 | 0.66 | 0.12 | 0.53 |
| 8 | 0.88 | 0.12 | 0.50 |
| 9 | 0.88 | 0.12 | 0.40 |

The RMS granularity of each element was determined by the method described in the *Theory of the Photographic Process*, 4th Edition, edited by T H James, p 619, using a scanning aperture of 48 microns. Elements 5 and 7 showed less granularity, particularly at higher density, than control Elements 6, 8 and 9.

Although the invention has been described in considerable detail with particular reference to certain preferred embodiments thereof, variations and modifications can be effected within the spirit and scope of the invention.

We claim:

1. A photographic element comprising a support and a photosensitive silver halide emulsion having associated therewith a dye-forming coupler having the structure:

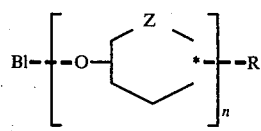

wherein:
Z represents the atoms to complete, with the attached oxygen atom, the same 5-pyrazolone magenta dye-forming coupler moiety, phenol cyan dye-forming coupler moiety or naphthol cyan dye-forming coupler moiety, the * in the ring completed by Z representing the coupling position;
R is hydrogen or a coupling-off group;
Bl is a blocking group removable, during development, from the coupler moiety completed by Z to which it is directly attached, thereby to activate the coupling position of the coupler moiety; and
n is an integer of 2 to 4.

2. A photographic element of claim 1 wherein the dye-forming coupler has the structure:

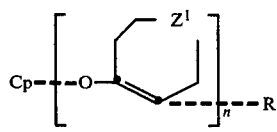

wherein:
$Z^1$ represents the atoms to complete, with the attached oxygen atom, a 5-pyrazolone magenta dye-forming coupler moiety;
R is hydrogen or a coupling-off group;
n is an integer of 2 to 4; and
Cp is a coupler moiety which, upon reaction with oxidized color-developing agent, yields a colorless or alkalisoluble reaction product.

3. A photographic element of claim 1 wherein the dye-forming coupler has the structure:

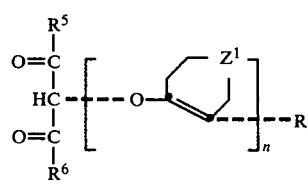

wherein:

$Z^1$ represents the atoms to complete, with the attached oxygen atom, a 5-pyrazolone magenta dye-forming coupler moiety;
R is hydrogen or a coupling-off group;
n is an integer of 2 to 4; and
$R^5$ and $R^6$ represent the atoms to complete an alkalisoluble yellow dye-forming coupler moiety.

4. A photographic silver halide emulsion containing a dye-forming coupler having the structure:

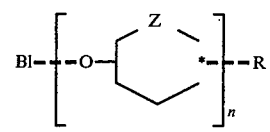

wherein:
Z represents the atoms to complete, with the attached oxygen atom, the same 5-pyrazolone magenta dye-forming coupler moiety, phenol cyan dye-forming coupler moiety or naphthol cyan dye-forming coupler moiety, the * in the ring completed by Z representing the coupling position;
R is hydrogen or a coupling-off group;
Bl is a blocking group removable, during development, from the coupler moiety completed by Z to which it is directly attached, thereby to activate the coupling position of the coupler moiety; and
n is an integer of 2 to 4.

5. A photographic emulsion of claim 4 wherein the dye-forming coupler has the structure:

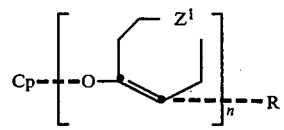

wherein:
$Z^1$ represents the atoms to complete, with the attached oxygen atom, a 5-pyrazolone magenta dye-forming coupler moiety;
R is hydrogen or a coupling-off group;
n is an integer of 2 to 4; and
Cp is a coupler moiety which, upon reaction with oxidized color-developing agent, yields a colorless or alkalisoluble reaction product.

6. A photographic emulsion of claim 4 wherein the dye-forming coupler has the structure:

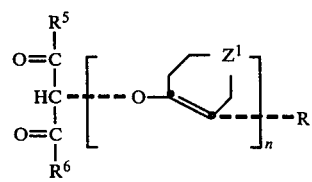

wherein:
$Z^1$ represents the atoms to complete, with the attached oxygen atom, a 5-pyrazolone magenta dye-forming coupler moiety;
R is hydrogen or a coupling-off group;
n is an integer of 2 to 4; and
$R^5$ and $R^6$ represent the atoms to complete an alkalisoluble yellow dye-forming coupler moiety.

7. A process of forming a dye image in a photographic element comprising a support and a silver halide emulsion, comprising the step of developing the element with a silver halide color-developing agent in the presence of a dye-forming coupler having the structure:

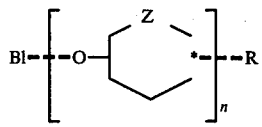

wherein:

Z represents the atoms to complete, with the attached oxygen atom, the same 5-pyrazolone magenta dye-forming coupler moiety, phenol cyan dye-forming coupler moiety or naphthol cyan dye-forming coupler moiety, the * in the ring completed by Z representing the coupling position;

R is hydrogen or a coupling-off group;

Bl is a blocking group removable, during development, from the coupler moiety completed by Z to which it is directly attached, thereby to activate the coupling position of the coupler moiety; and n is an integer of 2 to 4.

8. A process of claim 7 wherein the color-developing agent is p-phenylenediamine.

* * * * *